United States Patent [19]

Eagon et al.

[11] Patent Number: 4,555,022
[45] Date of Patent: Nov. 26, 1985

[54] PEEL PACKAGE STERILE SANITARY PADS

[76] Inventors: Vicki L. Eagon, 5762 Haney Dr., Watauga, Tex. 76148; Towanda S. Showers, High Meadow Dr., Lt. 40, Fort Worth, Tex.

[21] Appl. No.: 577,375

[22] Filed: Feb. 6, 1984

[51] Int. Cl.⁴ .................. B65B 83/00; B65D 75/00
[52] U.S. Cl. .................. 206/440; 206/438; 206/441
[58] Field of Search ........... 206/440, 441, 438, 494, 206/812

[56] References Cited

U.S. PATENT DOCUMENTS

| | | | |
|---|---|---|---|
| 3,062,371 | 11/1962 | Patience | 206/440 |
| 3,148,771 | 9/1964 | Miller, Jr. | 206/440 |
| 3,217,871 | 5/1963 | Lee | 206/484.2 |
| 3,240,326 | 3/1966 | Miller | 206/812 |
| 3,326,450 | 6/1967 | Langdon | 206/438 |
| 3,335,719 | 8/1967 | Boucher | 206/494 |
| 3,652,006 | 3/1972 | Trewella | 206/440 |
| 3,698,549 | 10/1972 | Glassman | 206/440 |
| 3,717,244 | 2/1973 | Smith | 206/438 |
| 4,040,424 | 8/1977 | Hunt | 604/387 |
| 4,427,111 | 1/1984 | Laipply | 206/210 |

FOREIGN PATENT DOCUMENTS

| | | | |
|---|---|---|---|
| 663219 | 5/1963 | Canada | 206/440 |
| 1339399 | 12/1973 | United Kingdom | 206/440 |

Primary Examiner—William T. Dixson, Jr.
Assistant Examiner—Brenda J. Ehrhardt
Attorney, Agent, or Firm—Richards, Harris, Medlock & Andrews

[57] ABSTRACT

A sanitary pad package (10) is disclosed which includes a backing sheet (12) and a sterilizable absorbent sanitary pad (18). A peelable adhesive (24) is provided to enclose the sanitary pad (18) when the backing sheet (12) is folded about the midfold line (26). The peelable adhesive (24) includes an adhesive coating (28) and a coating (30) having openings (32) therethrough exposing the backing sheet (12). The adhesive coating (28) is activated so that the coating (28) enters the openings (32) to adhere to the backing sheet (12).

2 Claims, 4 Drawing Figures

PEEL PACKAGE STERILE SANITARY PADS

TECHNICAL FIELD

This invention relates to the packaging of sterile materials, and in particular to sterile sanitary pads.

BACKGROUND OF THE INVENTION

Sterile sanitary pads are widely employed, both in hospitals and in the home. The pads can be maturity, surgical, hemorrhoid, or feminine hygiene pads, for example, with or without an adhesive backing for securing to the body. U.S. Pat. No. 4,040,424, issued to James R. Hunt on Aug. 9, 1977 discloses one type of sanitary pad which is designed to be enclosed by an outer envelope to maintain sterility prior to use.

Heretofore, sterile sanitary pads have typically been packaged in a sealed paper wrapping which is sealed at the top and bottom of the wrapping and down the middle of the wrapping. The paper wrapping does not allow easy handling of the package while opening and can easily result in contamination of the wrapped pad.

In opening a conventional paper wrapped sanitary pad, one end of the package must be torn open initially. The package must then be torn down the side, which can result in contamination of the pad and, in one example in the hospital environment, an inability to place the pad on a sterile surgical field because of the loss of sterility.

In the hospital environment, the time consuming and difficult task of opening the conventional paper package in an attempt to preserve its sterility increases the "turn over time" in surgery. The "turn over time" is the time allotted between the end of one surgical case and the beginning of another surgical case. This time would include the time necessary to remove a patient, clean up the surgical area and prepare the next patient for surgery. Naturally, it is not possible to perform any surgical procedures during this period and therefore the facilities of the hospital and the time of the surgeon is wasted. It is therefore desirable to minimize this "turn over time", while maintaining professional standards.

Outside the hospital environment, the time and effort necessary to open the conventional paper package can be excessive. This is particularly true in the use of maturity pads where an elderly patient may have trouble even opening the package, particularly to maintain the sterility of the pad.

A need therefore exists for an improved packaging technique for sanitary pads which makes the package easier and faster to open than currently available designs while further permitting better control and maintenance of the sterility of the pad while opening the package and placing the pad in the necessary location. These advantages will reduce the "turn over time" in hospital environments and provide a cost reduction to the patient.

SUMMARY OF THE INVENTION

In accordance with one aspect of the present invention, a sanitary pad package is disclosed. The sanitary pad package includes a backing sheet and a sterilizable absorbant sanitary pad secured on a first side of the backing sheet. The backing sheet extends beyond the edges of the sterilizable absorbant sanitary pad. A continuous strip of peelable adhesive is secured on the first side of the backing sheet and extends about the periphery of the sterilizable absorbant sanitary pad so that the backing sheet can be folded to bring portions of the strip of peelable adhesive into facing relationship to form a continuous seal about the periphery of the sterilizable absorbant sanitary pad to enclose the sterilizable absorbant sanitary pad in the backing sheet so that the sterility of the pad can be maintained prior to and during opening of the pad.

BRIEF DESCRIPTION OF THE DRAWINGS

A more complete understanding of the invention may be had by reference to the following Detailed Description when taken in conjunction with the accompanying Drawings, wherein.

DETAILED DESCRIPTION

Figure 1:
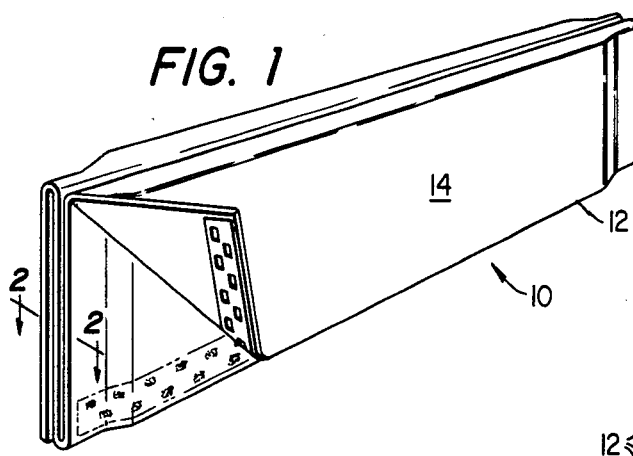
FIG. 1 is a perspective view of a sanitary pad package forming the first embodiment of the present invention.

Referring now to the drawings, wherein like reference characters designate like or corresponding parts throughout several views, FIG. 1 illustrates a sanitary pad package 10 forming a first embodiment of the present invention.

As can be seen in FIGS. 1–4, the sanitary pad package 10 includes a backing sheet 12 having a generally rectangular configuration with a first side 14 and a reverse side 16. The backing sheet 12 is preferably formed of a sterilizable material and a material that will prevent contamination, such as bacteria, from passing therethrough so that an object wrapped within the backing sheet 12 will maintain sterility.

The sanitary pad package 10 further includes a sterilizable absorbant sanitary pad 18 which is secured on the first side 14 of the backing sheet 12 by a suitable adhesive. The sanitary pad 18 is intended for absorption in maturity, surgical, hemorrhoid and feminine hygiene applications, as well as other uses. As can readily be seen from FIG. 3, the pad 18 is generally positioned in the center of the first side 14 of backing sheet 12 and the first side 14 extends outwardly from the outer periphery 20 of the sanitary pad 18 in all directions.

Figure 3:
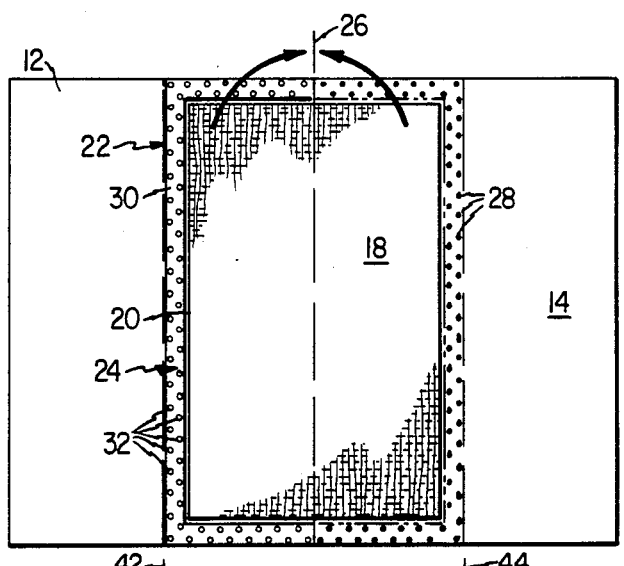
FIG. 3 is a plan view of the first side of the backing sheet of the sanitary pad package illustrating the absorbant sanitary pad.

The sanitary pad package 10 further includes a continuous strip 22 of a peelable adhesive 24. Such a peelable adhesive is disclosed and claimed in U.S. Pat. No. 3,217,871, issued to R. L. Lee on Nov. 16, 1965 which disclosure is herein incorporated by reference. The peelable adhesive 24 is formed of two major components, separated by the mid-fold line 26 of the sanitary pad package 10. On the left side of the mid-fold line 26 as seen in FIG. 3, the peelable adhesive 24 comprises an adhesive coating 28, preferably of a thermo-responsive material. On the right side of mid-fold line 26 as seen in FIG. 3, the peelable adhesive 24 comprises a coating 30 having spaced openings 32 extending through the coating 30 and exposing portions of the first side 14 of the backing sheet 12.

Figure 2:
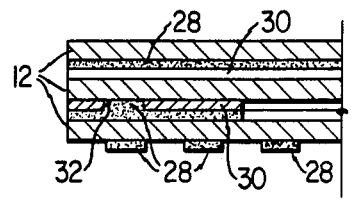
FIG. 2 is a partial cross section of the sanitary pad package shown in FIG. 1 taken along line 2—2 in FIG. 1 in the direction of the arrows.

When the sanitary pad package 10 is folded along the mid-fold line 26 as indicated by arrows 34 in FIG. 3, the portions of the adhesive coating 28 and coating 30 move into a facing and abutting relationship. The adhesive coating 28 is then activated, either thermally or by another means so that the adhesive coating 28 flows into the openings 32 in the coating 30 to adhere to the first side 14 of the backing sheet 12 as best seen in FIG. 2. While the adhesive coating 28 can also be designed to adhere to the surface of the coating 30, this adherance, if present, is preferably very slight.

One significant advantage of the use of the adhesive coating 28 and coating 30 is the large resistence to separation of the folded package when forces are applied parallel the length of the coatings 28 and 30 but the relatively slight force necessary to separate and open the sanitary package to expose the sanitary pad 18 when forces are exerted transverse the length of the coatings 28 and 30. The material forming coating 28 is preferably one of the same materials which are disclosed in U.S. Pat. No. 3,217,871 to form the coating 17 disclosed in the patent. These materials include polyethylene, polypropylene, polyvinyl acetate-chloride copolymer and a polyvinylidene chloride. The material forming coating 30 is also preferably one of the same materials as suggested in U.S. Pat. No. 3,217,871 to form the coating 18 disclosed in that patent. These materials include (a) polyvinyl acetatechloride copolymer 17.5%, mixed fatty amides 7.5%, and methyl ethyl ketone 75%; (b) polyvinyl acetatechloride copolymer (VYNS) 15.0%, polyvinyl acetatechloride copolymer (VYHH) 8.75%, mixed fatty amides 1.25% and 2-nitropropane 75.00%; (c) 18/25 cps. RS nitrocellulose 24.0%, polymethyl acrylate 8.0%, zinc stearate 3.0%, methyl ethyl ketone, 50.0% and isopropyl alcohol 15.0%, (d) cyclized rubber (Pliolite S-7) 10.0%, paraffin wax 6.0%, dimerized resin acids (Dymerex) 4.0% and toluene 80.0%; (e) cellulose acetate butyrate 9.80%, urea formaldehyde resin 16.30%, sucrose ester 11.30%, polymethyl styrene 6.40%, eopxy resin (Epon 836) 4.00%, silicone oil 0.05%, p-toluenesulfonic acid/n-butanol (50:50) 0.65%, toluene 24.30%; ethyl alcohol 16.70% and isobutyl alcohol 10.50%. All proportions in the foregoing formulations being by weight.

Figure 4:
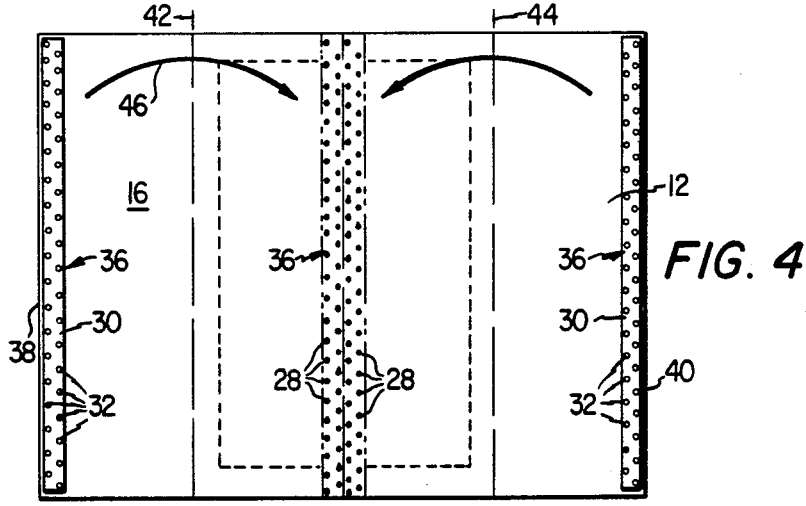
FIG. 4 is a plan view of the opposite side of the backing sheet of the sanitary pad package.

A peelable adhesive 36 is also preferably positioned along the outer edges 38 and 40 of the backing sheet 12 and on both sides of the mid-fold line 26 on the reverse side 16 of the backing sheet 12 as best seen in FIG. 4. The peelable adhesive 36 is again formed of the two coatings 28 and 30. As seen in FIG. 4, the adhesive coating 28 is positioned on both sides of the mid-fold line 26. The coating 30 is positioned along the outer edges 38 and 40.

As can readily be seen in FIGS. 1 and 4, the backing sheet 12 can be folded along intermediate fold lines 42 and 44 in the direction of arrows 46 as seen in FIG. 4. The adhesive coating 28 can then be activated to flow into the openings 32 and the coatings 30 to secure the outer edges 38 and 40 to the area adjacent the mid-fold line 26. Adhesive coating 28 can also be made of a discontinuous character as seen in FIGS. 1 and 2. However, the areas of adhesive coating 28 should overlap the edges of the opening 32 facing the coating 28 to insure adequate penetration of coating 28 to form a seal.

The sanitary pad package 10 of the present invention permits much easier and faster opening of the package to expose the sanitary pad 18 for use. This feature permits reduction of the possibility for contamination of the pad during opening. The sanitary pad package 10 is simpler for elderly people to open when the sanitary pad 18 is used for a maturity patient. The "turn over time" in surgical areas can be reduced by use of the sanitary pad package 10 with resultant cost savings and decreased chance of contamination.

Although a single embodiment of the invention has been illustrated in the accompanying Drawings and described in the foregoing Detail Description, it will be understood that the invention is not limited to the embodiment disclosed, but is capable of numerous rearrangements, modifications and substitutions of parts and elements without departing from the spirit of the invention.

We claim:

1. A sanitary pad package comprising:

a sterilizable, single layer backing sheet;

a dry sterilizable absorbent sanitary pad secured on a first side of the backing sheet, the backing sheet extending beyond the edges of the sanitary pad, the backing sheet and sterilizable absorbent sanitary pad being sterilizable for use of the sanitary pad package within a sterile field;

a continuous strip of peelable adhesive secured on the first side of the backing sheet and extending about the periphery of the sanitary pad so that the backing sheet can be folded to bring portions of the strip of peelable adhesive into facing relationship to form a continuous seal about the periphery of the sanitary pad to enclose the sanitary pad in the backing sheet so that the sterility of the sanitary pad can be maintained prior to enduring opening of the sanitary pad package, the peelable adhesive eliminating the need to tear the backing sheet to open the sanitary pad package, thereby reducing the time and effort needed to open the sanitary pad package while maintaining the sterility of the sterilizable absorbent sanitary pad; and strips of peelable adhesive secured on the opposite side of the backing sheet and the backing sheet is folded along intermediate fold lines outward from the continuous seal to form a compact package.

2. A sanitary pad package comprising:

a generally rectangular sterilizable, single layer backing sheet of paper having first and second sides being foldable along a midline fold and first and second intermediate folds on either side of the midline fold;

a dry sterilizable absorbent sanitary pad secured on a first side of the backing sheet and inside the intermediate fold lines, the backing sheet extending beyond the edges of the sanitary pad about the entire periphery of the sanitary pad, the backing sheet and sterilizable absorbent sanitary pad being sterilizable to permit the use of the sanitary pad package in a sterile surgical field, the backing sheet being fluid permeable to allow initial sterilization and resterilization of the sanitary pad package;

a continuous strip of peelable adhesive secured on the first side of the backing sheet and extending about the periphery of the sanitary pad and between the intermediate folds so that the backing sheet can be folded about the midline fold to bring portions of the strip of peelable adhesive into facing relationship to form a continuous seal about the periphery of the sanitary pad to enclose the sanitary pad in the backing sheet so that the sterility of the pad can be maintained prior to and during opening of the sanitary pad package, the peelable adhesive on a first side of the midline fold being formed of an activatable adhesive coating, the peelable adhesive on the opposite side of the midline fold being formed by a second coating having a plurality of spaced openings therethrough exposing the first side of the backing sheet, the adhesive coating being activatable to enter the openings through the second coating and adhere to the first side of the backing sheet to form the continuous seal; and strips of peelable adhesive positioned at the outer edges of the backing sheet on the second side of the backing sheet and near the midline fold of the second side of the backing sheet so that as the backing sheet is folded around the intermediate fold lines, the outer edges are adhesively attached near the mid-fold line to form a compact package, the peelable adhesive avoiding the need to tear the backing sheet to open the sanitary pad package and thus reducing the time and effort needed to open the sanitary pad package while maintaining the sterility of the sterilizable absorbent sanitary pad.

* * * * *

UNITED STATES PATENT AND TRADEMARK OFFICE
CERTIFICATE OF CORRECTION

PATENT NO. : 4,555,022
DATED : November 26, 1985
INVENTOR(S) : Vicki L. Eagon and Towanda S. Showers It is certified that error appears in the above-identified patent and that said Letters Patent is hereby corrected as shown below:

In the Abstract - Line 2, change "absorbant" to --absorbent--.
Column 1, line 63, change "absorbant" to --absorbent--.
Column 1, line 65, change "absorbant" to --absorbent--.
Column 1, line 68, change "absorbant" to --absorbent--.
Column 2, line 4, change "absorbant" (both occurrences) to --absorbent--.
Column 2, line 20, change "absorbant" to --absorbent--.
Column 2, line 41, change "absorbant" to --absorbent--.
Column 2, line 57, change "left" to --right--.
Column 2, line 60, change "right" to --left--.
Column 3, line 22, change "18" to --30--.

Signed and Sealed this

Twenty-fifth Day of February 1986

[SEAL]

Attest:

DONALD J. QUIGG

Attesting Officer    Commissioner of Patents and Trademarks